United States Patent [19]

Höelderich et al.

[11] Patent Number: 4,554,142
[45] Date of Patent: Nov. 19, 1985

[54] PROCESS FOR THE PREPARATION OF BOROSILICATE ZEOLITES

[75] Inventors: Wolfgang Höelderich; Wolf D. Mross, both of Frankenthal; Matthias Schwarzmann, Limburgerhof, all of Fed. Rep. of Germany

[73] Assignee: BASF Aktiengesellschaft, Fed. Rep. of Germany

[21] Appl. No.: 433,899

[22] Filed: Oct. 12, 1982

[30] Foreign Application Priority Data

Oct. 15, 1981 [DE] Fed. Rep. of Germany ....... 3140895

[51] Int. Cl.$^4$ ............................................. C01B 35/10
[52] U.S. Cl. ................................. 423/277; 423/326; 423/328; 423/329; 502/77; 502/202
[58] Field of Search ............... 423/277, 328, 329, 326; 502/77, 202; 352/455 Z

[56] References Cited

U.S. PATENT DOCUMENTS

| | | | |
|---|---|---|---|
| 4,268,420 | 5/1981 | Klotz | 252/432 |
| 4,269,813 | 5/1981 | Klotz | 423/277 |
| 4,292,457 | 9/1981 | Klotz | 585/447 |
| 4,292,458 | 9/1981 | Klotz | 585/469 |
| 4,377,502 | 3/1983 | Klotz | 423/328 |
| 4,401,637 | 8/1983 | Marosi et al. | 423/328 |
| 4,431,621 | 2/1984 | Taramasso et al. | 423/329 |
| 4,495,303 | 1/1985 | Kuehl | 423/328 |

FOREIGN PATENT DOCUMENTS

| | | | |
|---|---|---|---|
| 0054387 | 6/1982 | European Pat. Off. | 252/455 Z |
| 2746790 | 4/1978 | Fed. Rep. of Germany . | |
| 0051741 | 5/1982 | Fed. Rep. of Germany | 423/329 |
| 0140023 | 11/1981 | Japan | 502/60 |
| 0007821 | 1/1982 | Japan | 252/455 Z |
| 0011819 | 1/1982 | Japan | 252/455 Z |
| 20333358 | 5/1980 | United Kingdom | 423/328 |
| 2062603 | 5/1981 | United Kingdom | 423/277 |
| 2132993 | 7/1984 | United Kingdom | 423/328 |

OTHER PUBLICATIONS

Peter A. Jacobs, "Properties of the End Members in the Pentasil Family of Zeolites: Characterization as Absorbents", *Zeolites*, 1981, vol. 1, pp. 161-168.
G. T. Kokotailo et al, "Pentasil Family of High Silica Crystalline Materials", Chem. Soc. Spec. Publ., 1979, 33, pp. 133-139.

*Primary Examiner*—John Doll
*Assistant Examiner*—Jackson Leeds
*Attorney, Agent, or Firm*—Keil & Weinkauf

[57] ABSTRACT

Novel crystalline ZBH borosilicate zeolites of the pentasil type are prepared by hydrothermal crystallization of silicon dioxide and boric acid in the presence of alkali metal salts, at from 80° to 140° C. in an ethereal or aqueous-ethereal mixture.

8 Claims, No Drawings

PROCESS FOR THE PREPARATION OF BOROSILICATE ZEOLITES

The present invention relates to novel ZBH borosilicate zeolites and to a process for the preparation of crystalline ZBH borosilicate zeolites of the pentasil type in a pure or aqueous etherel medium, without the use of amines, and to the use of the products as catalysts for converting methanol or dimethyl ether to lower olefins.

Boron zeolites have hitherto not been found in nature. They can only be obtained synthetically (German Laid-Open Application DOS No. 2,746,790). Aluminum-containing zeolite materials, both of natural and of synthetic origin, have proved catalytically active in various types of hydrocarbon conversions, for example in hydrocarbon cracking technology, and are also used industrially as ion exchangers and molecular sieves.

In general, zeolites have a highly ordered structure with a rigid three-dimensional lattice of $SiO_4$ and $MeO_4$ tetrahedra, Me being, for example, Al, Fe, Ga and B. These tetrahedra are linked by shared oxygen atoms and the ratio of Si and Me atoms to oxygen is 1:2.

The electrovalency of the tetrahedra containing the trivalent element Me is balanced by inclusion of cations, for example alkali metal cations or hydrogen ions, in the crystal. Cation exchange is feasible. Before drying or calcining, the voids between the tetrahedra are occupied by water molecules.

In recent years, crystalline aluminosilicates having a high $SiO_2/Al_2O_3$ ratio, namely $\geq 11$, have aroused increasing interest. Such zeolites have a pentasil structure and are distinguished by great heat stability and extremely high acidity. They are synthesized in a conventional manner from a silicon component and an aluminum component in the presence of bulky quaternary organic ammonium or phosphonium compounds and alkali metal compounds as mineralizing agents. Such a process is described in U.S. Pat. No. 3,702,886. The large ammonium or phosphonium ions are intended to serve as a template for the desired zeolite structure and permit the synthesis of aluminum zeolites having $SiO_2/Al_2O_3$ ratios of, for example, from 100 to 3000.

Boron zeolites having a pentasil structure have hitherto only been prepared in the presence of amines (German Laid-Open Application DOS No. 2,746,790). The use of the quaternary amines presents technical problems.

We have found that novel ZBH borosilicate zeolites of the pentasil type are obtained by hydrothermal crystallization of silicon dioxide and boric acid in the presence of alkali metal salts if the crystallization is carried out at from 80° to 140° C. in an ethereal or aqueous-ethereal mixture.

In a preferred embodiment of the preparation of these amine-free ZBH borosilicate zeolites a reaction mixture of $SiO_2$, for example a commercial pyrogenic silica, $H_3BO_3$ and NaOh is reacted in a 50:50 (by weight) ether/water mixture for from 5 to 7 days at 110°–130° C. in a stirred autoclave under autogenous pressure. The reaction product first obtained may, before calcining, contain ether in place of the $H_2O$ molecules in the intracrystalline pores. All residues of organic compounds are removed by drying and calcining, so that only the free alkali metal ions remain in the zeolite.

The molar ratio of $SiO_2$ to $B_2O_3$ in the reaction mixture is from 3 to 300, preferably from 10 to 50.

The proportion of alkali metal hyroxide is from 1 to 3 moles, preferably about 1.7 moles, per molar equivalent of $B_2O_3$.

Advantageously, nucleating crystals are added to control and accelerate the reaction.

The solvents used are the general category of ethers, including linear and cyclic esters containing a ($-CH_2-CH_2-O-$) group, e.g. monoethylene, diethylene, triethylene and tetraethylene glycol dimethyl ether, diethyl ether, tetrahydrofuran, dioxane or a mixture of triethylene to decaethylene glycol methyl isopropyl ether having a mean degree of oxyethylation of 5.5 and hence an average formula of $CH_3O-(CH_2-CH_2-O)_{5.5}-C_3H_7$, diethylene glycol methyl isopropyl ether or a mixture of polyethylene glycol methyl isopropyl ethers having a mean degree of oxyethylation of 5.5 and hence the average formula $CH_3O(-CH_2-CH_2-O)_{5.5}$, or a mixture of oxyethylated oxo-alcohols having a mean molecular weight of 200, 600 or 6,000, as well as linear ethers containing a ($CH_3-CH-CH_2-O$) group, and linear ethers containing a ($-CH_2-O$) group, e.g. dimethoxymethane. The glymes give particularly well-formed crystals of the ZBH-boron zeolites, of size 1–5 $\mu$m. This is a further advantage of the novel method of preparation in ethers.

The molar composition of the reaction mixture is set to conform to the following values:
$SiO_2/B_2O_3 = 3-300$, preferably 10–50
$M_2O/B_2O_3 = >1$, preferably 1.3–2
$ROR/B_2O_3 = 18-390$
wherein M is an alkali metal, especially Na, and ROR is an ether. The concentration of the ether in $H_2O$ may be from 10 to 100% by weight, preferably 50% by weight.

The process according to the invention is carried out at reaction temperatures of from 80° to 140° C., preferably from 110° to 130° C., advantageously under autogenous pressure in a stainless steel stirred autoclave for from 3 to 7 days.

After the reaction, the product is advantageously filtered off, washed thoroughly with water and dried at 110° C. for 16 hours. It is then calcined at 550° C. for 20 hour in order to burn off the ether still occluded, and dehydrate the zeolite. The alkali metal form of the zeolite can be converted to the catalytically active H form by conventional exchange methods, for example using ammonium salts. The mother liquor separated off can be re-used in subsequent syntheses.

The general formula of the ZBH borosilicate zeolites prepared by the method of the invention is:

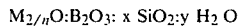

$M_{2/n}O:B_2O_3: x\ SiO_2:y\ H_2O$ where M is one or more cations of valency n, x is $\geq 10$ and y is from 0 to 80.

The ZBH borosilicate zeolites prepared in ether, in accordance with the invention, exhibit the following important X-ray diffraction lines:

TABLE 1

| Interplanar spacing d (Å) | Relative intensity I/I° | Interplanar spacing d (Å) | Relative intensity I/I° |
|---|---|---|---|
| 11.0746 ± 0.15 | 100 | 2.9259 | 7 |
| 9.9725 | 68 | 2.8543 | 4 |
| 9.7271 | 19 | 2.7151 | 5 |
| 6.6567 | 10 | 2.5928 | 5 |
| 6.3220 | 17 | 2.4984 | 3 |
| 5.9489 ± 0.1 | 22 | 2.4746 | 5 |
| 5.6740 | 11 | 2.4013 | 4 |
| 5.0022 | 10 | 2.3106 | 3 |

TABLE 1-continued

| Interplanar spacing d (Å) | Relative intensity I/I° | Interplanar spacing d (Å) | Relative intensity I/I° |
|---|---|---|---|
| 4.9479 | 10 | 1.9999 | 10 |
| 4.5883 | 8 | 1.9825 | 9 |
| 4.3352 | 10 | 1.9418 | 3 |
| 4.2392 | 11 | 1.9062 | 3 |
| 3.9747 ± 0.07 | 5 | 1.8621 | 5 |
| 3.8322 | 96 | 1.8289 | 3 |
| 3.7980 | 70 | 1.7576 | 3 |
| 3.7282 | 30 | 1.6615 | 3 |
| 3.6940 | 46 | 1.6544 | 3 |
| 3.6254 | 25 | 1.6501 | 3 |
| 3.4652 | 5 | 1.4807 | 3 |
| 3.4174 | 9 | 1.4539 | 4 |
| 3.3654 | 6 | 1.4377 | 4 |
| 3.3371 | 10 | 1.4149 | 4 |
| 3.2907 | 10 | 1.4046 | 3 |
| 3.2429 | 3 | 1.3864 | 4 |
| 3.1188 | 4 | 1.3738 | 4 |
| 3.0303 | 12 | 1.3556 | 3 |
| 2.9691 | 13 | | |

The X-ray diffraction diagram is recorded using an automatic APO-10 powder diffractometer. Copper radiation, and a graphite monochromator, are used.

The X-ray diffraction pattern typical for the ZBH borosilicate zeolites prepared in ether proves these products to be members of the pentasil family.

In the novel ZBH borosilicate zeolites the boron is built into the tetrahedral lattice positions of the crystal. The incorporation of boron into the crystal lattice manifests itself in a shift in the X-ray diffraction lines towards smaller d-values compared to corresponding aluminosilicate zeolites (Table 2); the length of a B—O bond is substantially shorter than the Al—O spacing. Hence, incorporating boron into the crystal lattice results in a contraction of the unit cell, i.e. a shift in the d spacings to smaller values compared to the corresponding aluminosilicate zeolites or compared to the silicalite.

A comparison of the lattice plane spacings of the novel boron zeolites with those of ZSM-5 shows that the d values (Å) in the former are smaller than in the latter (cf. Table 2).

TABLE 2

| ZBH | | ZBH | |
|---|---|---|---|
| d | I/I | d | I/I |
| 11.0746 | 100 | 2.9259 | 7 |
| 9.9725 | 69 | 2.8543 | 4 |
| 9.7271 | 19 | 2.7151 | 5 |
| 6.6567 | 10 | 2.5928 | 5 |
| 6.3220 | 17 | 2.4984 | 3 |
| 5.9489 | 22 | 2.4746 | 5 |
| 5.6740 | 11 | 2.4013 | 4 |
| 5.5405 | 18 | 2.3831 | 5 |
| 5.0022 | 10 | 2.3106 | 3 |
| 4.9479 | 10 | 1.9999 | 10 |
| 4.5883 | 8 | 1.9825 | 9 |
| 4.3352 | 10 | 1.9418 | 3 |
| 4.2392 | 11 | 1.9062 | 3 |
| 3.9747 | 5 | 1.8621 | 5 |
| 3.8322 | 96 | 1.8289 | 3 |
| 3.7980 | 70 | 1.7567 | 3 |
| 3.7282 | 30 | 1.6615 | 3 |
| 3.6940 | 46 | 1.6544 | 3 |
| 3.6254 | 25 | 1.6501 | 3 |
| 3.4652 | 5 | 1.4807 | 3 |
| 3.4174 | 9 | 1.4539 | 4 |
| 3.3654 | 6 | 1.4377 | 4 |
| 3.3371 | 10 | 1.4149 | 4 |
| 3.2907 | 10 | 1.4046 | 3 |
| 3.2429 | 3 | 1.3864 | 4 |
| 3.1188 | 4 | 1.3738 | 4 |
| 3.0303 | 12 | 1.3556 | 3 |
| 2.9691 | 13 | | |

TABLE 2-continued

| ZSM-5[1] | | AMS-1 B[2] | |
|---|---|---|---|
| d(Å) | I | d (Å) | Relative Intensity |
| 11.36 | s | 11.3 ± 0.2 | 38 |
| 10.20 | ms | 10.1 ± 0.2 | 30 |
| 9.90 | — | 6.01 ± 0.07 | 14 |
| 9.14 | vw | 4.35 ± 0.05 | 11 |
| 7.54 | w | 4.26 ± 0.05 | 14 |
| 7.17 | w | 3.84 ± 0.05 | 100 |
| 6.79 | vw | 3.72 ± 0.05 | 52 |
| 6.06 | w | 3.65 ± 0.05 | 31 |
| 5.77 | w | 3.44 ± 0.05 | 14 |
| 5.63 | w | 3.33 ± 0.05 | 16 |
| 5.42 | vw | 3.04 ± 0.05 | 16 |
| 5.19 | vw | 2.97 ± 0.02 | 22 |
| 5.05 | w | 2.48 ± 0.02 | 11 |
| 4.65 | w | 1.99 ± 0.02 | 20 |
| 4.40 | w | 1.66 ± 0.02 | 12 |
| 4.30 | w | | |
| 4.12 | vw | | |
| 4.04 | vw | | |
| 3.84 | vs | | |
| 3.74 | vs | | |
| 3.62 | s | | |
| 3.50 | w | | |
| 3.46 | w | | |
| 3.33 | w | | |
| 3.27 | vw | | |
| 3.07 | w | | |
| 3.00 | m | | |

[1] Zeolites and molecular sieves, Donald W. Breck, Wiley-Interscience Publishers, page 373 (1974)
[2] German Laid-Open Application DOS 2,746,790, Standard Oil Co.

The crystalline ZBH borosilicate zeolites described here differ clearly in respect of their interplanar spacings (d values in Å) from those of boron zeolite AMS - 1 B of Standard Oil Co. (Table 2).

A comparison of the intensities of the X-ray diffraction lines also reveals substantial differences. The differences in both d values and intensities prove that the ZBH borosilicates are novel zeolites.

It is true that the ZBH borosilicate zeolites prepared in ethers belong, in respect of structural type, to the pentasil family, but compared to the other members of this structural type they exhibit markedly different X-ray diffraction lines and hence different lattice spacings.

The zeolites, obtained in H form after exchange, can be extruded together with a matrix material and be employed as catalysts for hydrocarbon conversions such as isomerizations, cracking and conversion of alcohols and ethers.

The analytical data in the Examples relate to dry material. The substances are calcined for 20 h at 550° C. before chemical analysis. The difference from 100% is accounted for by adsorbed water.

EXAMPLES 1-6

80 g of aerosil are stirred into 1,000 g of a 50:50 ether/$H_2O$ mixture at about 40° C. 15.2 g of $H_3BO_3$ are dissolved in 200 g of the ether/$H_2O$ mixture and the two solutions are then combined. 14.7 g of NaOH are then added, followed, if desired, by nucleating crystals. The mixture, stirred to homogenize it, is reacted for 5 days at from 80° 140° C. in a stirred autoclave under autogenous pressure. It is then cooled and the crystalline product is filtered off, washed with 10 liters of water, dried for 16 hours at 110° C. and calcined for 20 hours at 500° C.

The results of Examples 1 to 6, employing different solvents, are summarized in Table 3. The synthetic boron zeolites were obtained free from impurities.

Table 4 shows the series of Examples and the X-ray diffraction diagrams of the zeolites, as obtained using various solvents.

EXAMPLE 7-8

Examples 7 and 8 (Table 5) show the results of preparing crystalline boron-aluminosilicates in diethylene glycol dimethyl ether, using various $SiO_2/B_2O_3$ ratios.

TABLE 3

| Example | Ether | $SiO_2/B_2O_3$ ratio employed | % $SiO_2$ found | % $B_2O_3$ found | $SiO_2/B_2O_3$ found | % Na found |
|---|---|---|---|---|---|---|
| 1 | Ethylene glycol dimethyl ether | 11 | 86.6 | 4.58 | 22.1 | 4.3 |
| 2 | Diethylene glycol dimethyl ether | 11 | 87.6 | 3.5 | 29.2 | 3.1 |
| 3 | Triethylene glycol dimethyl ether | 11 | 79.7 | 8.28 | 11.3 | 7.2 |
| 4 | Tetraethylene glycol dimethyl ether | 11 | 89.3 | 3.6 | 29.0 | 4.0 |
| 5 | $CH_3O-(CH_2-CH_2-O)_{5.5}-C_3H_7$ | 11 | 92.8 | 1.17 | 92.6 | 3.05 |
| 6 | $CH_3O-(CH_2-CH_2-O)_2-C_3H_7$ | 11 | 85.0 | 6.18 | 16.0 | 3.86 |

TABLE 4

| Example 1 | | Example 2 | | Example 3 | | Example 4 | | Example 5 | | Example 6 | |
|---|---|---|---|---|---|---|---|---|---|---|---|
| d(Å) | I/I° | d(Å) | I/I° | d(Å) | I/I° | d(Å) | I/I° | d(Å) | I/I° | d(Å) | I/I° |
| 11.0239 | 92 | 11.0746 | 100 | 10.9615 | 65 | 10.8451 | 11 | 11.0877 | 82 | 10.9802 | 88 |
| 9.9244 | 65 | 9.9725 | 68 | 9.8165 | 52 | 9.9248 | 63 | 9.9659 | 66 | 9.8640 | 63 |
| 9.6520 | 22 | 9.7271 | 19 | 6.2778 | 17 | 9.6640 | 20 | 9.7499 | 20 | 6.6145 | 8 |
| 6.2968 | 15 | 6.6567 | 10 | 5.9070 | 18 | 6.6645 | 8 | 6.3307 | 15 | 6.2757 | 15 |
| 5.9453 | 17 | 6.3220 | 17 | 4.9255 | 14 | 6.3294 | 13 | 5.9459 | 19 | 5.9344 | 21 |
| 5.6705 | 12 | 5.9489 | 22 | 4.5591 | 15 | 5.9518 | 19 | 5.6699 | 10 | 5.6334 | 11 |
| 5.5216 | 15 | 5.6740 | 11 | 3.8114 | 100 | 5.6628 | 10 | 5.5449 | 14 | 5.5386 | 14 |
| 4.9889 | 9 | 5.5405 | 18 | 3.7773 | 74 | 5.5281 | 17 | 4.9861 | 10 | 5.0769 | 4 |
| 4.9403 | 8 | 5.0022 | 10 | 3.6831 | 54 | 4.9904 | 11 | 4.6151 | 9 | 4.9609 | 10 |
| 4.5789 | 10 | 4.9479 | 10 | 3.6514 | 22 | 4.9372 | 8 | 4.5917 | 11 | 4.9298 | 9 |
| 4.4317 | 6 | 4.5883 | 8 | 3.4392 | 34 | 4.5813 | 8 | 4.3479 | 17 | 4.5711 | 7 |
| 4.3356 | 12 | 4.3352 | 10 | 3.4083 | 38 | 4.5354 | 12 | 3.8365 | 100 | 4.3218 | 10 |
| 4.2248 | 13 | 4.2392 | 11 | 3.3848 | 32 | 3.9794 | 6 | 3.8026 | 63 | 4.2193 | 13 |
| 3.9758 | 6 | 3.9747 | 5 | 3.3482 | 37 | 3.8282 | 100 | 3.7027 | 46 | 3.9654 | 6 |
| 3.8218 | 100 | 3.8322 | 96 | 3.3178 | 34 | 3.7949 | 73 | 3.6328 | 25 | 3.8215 | 100 |
| 3.7928 | 71 | 3.7980 | 70 | 3.2976 | 27 | 3.6941 | 51 | 3.4261 | 20 | 3.7915 | 70 |
| 3.6911 | 50 | 3.7282 | 30 | 3.2803 | 24 | 3.6275 | 27 | 3.4055 | 20 | 3.6864 | 47 |
| 3.6255 | 29 | 3.6940 | 46 | 3.2514 | 20 | 3.4508 | 7 | 3.3895 | 19 | 3.6154 | 29 |
| 3.4524 | 9 | 3.6254 | 25 | 3.0179 | 18 | 3.4165 | 9 | 3.3754 | 9 | 3.4486 | 7 |
| 3.4173 | 12 | 3.4652 | 5 | 2.9612 | 18 | 3.3287 | 10 | 3.3538 | 30 | .4141 | 8 |
| 3.3517 | 12 | 3.4174 | 9 | 2.9443 | 16 | 3.2877 | 10 | 3.3330 | 25 | 3.3737 | 6 |
| 3.3237 | 14 | 3.3654 | 6 | 2.0532 | 8 | 3.0288 | 11 | 3.3207 | 21 | 3.3563 | 6 |
| 3.2935 | 13 | 3.3371 | 10 | 1.9936 | 12 | 2.9706 | 12 | 3.2989 | 20 | 3.3223 | 10 |
| 3.0295 | 12 | 3.2907 | 10 | 1.9718 | 10 | 2.9519 | 11 | 3.2763 | 14 | 3.2823 | 11 |
| 2.9667 | 14 | 3.2429 | 3 | 1.8542 | 8 | 2.9199 | 10 | 3.2483 | 11 | 3.0269 | 12 |
| 2.9206 | 11 | 3.1188 | 4 | 1.8369 | 9 | 2.8500 | 4 | 3.0278 | 9 | 2.9642 | 14 |
| 2.7145 | 6 | 3.0303 | 12 | 1.4508 | 5 | 2.5901 | 5 | 2.9764 | 14 | 2.9233 | 8 |
| 2.5969 | 5 | 2.9691 | 13 | | | 2.5490 | 3 | 2.9662 | 11 | 2.8453 | 3 |
| 2.4732 | 6 | 2.9259 | 7 | | | 2.4718 | 5 | 2.9224 | 9 | 2.7149 | 5 |
| 2.4015 | 5 | 2.8543 | 4 | | | 2.4023 | 4 | 2.7229 | 6 | 2.5863 | 5 |
| 2.3828 | 5 | 2.7151 | 5 | | | 2.3796 | 5 | 2.6015 | 6 | 2.4977 | 3 |
| 2.0536 | 3 | 2.5928 | 5 | | | 1.9984 | 11 | 2.4077 | 5 | 2.4717 | 5 |
| 1.9980 | 11 | 2.4984 | 3 | | | 1.9782 | 10 | 2.3915 | 5 | 2.4010 | 5 |
| 1.9766 | 11 | 2.4746 | 5 | | | 1.9401 | 3 | 2.3807 | 5 | 2.3777 | 5 |
| 1.9396 | 3 | 2.4013 | 4 | | | 1.9029 | 3 | 2.0022 | 10 | 2.3043 | 2 |
| 1.9059 | 3 | 2.3831 | 5 | | | 1.8613 | 4 | 1.9887 | 7 | 1.9984 | 11 |
| 1.8597 | 4 | 2.3106 | 3 | | | 1.8175 | 2 | 1.9834 | 8 | 1.9806 | 12 |
| 1.8421 | 3 | 1.9999 | 10 | | | 1.7582 | 2 | 1.8439 | 4 | 1.9432 | 3 |
| 1.8354 | 2 | 1.9825 | 9 | | | 1.7528 | 2 | 1.8397 | 4 | 1.9074 | 3 |
| 1.8179 | 2 | 1.9418 | 3 | | | 1.7446 | 3 | 1.8324 | 4 | 1.9016 | 3 |
| 1.7589 | 3 | 1.9062 | 3 | | | 1.6610 | 3 | 1.6628 | 4 | 1.8595 | 3 |
| 1.7464 | 3 | 1.8621 | 5 | | | 1.6507 | 3 | 1.6547 | 3 | 1.7613 | 2 |
| 1.6578 | 4 | 1.8289 | 3 | | | 1.6165 | 2 | 1.4565 | 4 | 1.7575 | 3 |
| 1.6504 | 4 | 1.7567 | 3 | | | 1.6010 | 3 | 1.4544 | 0 | 1.7538 | 0 |
| 1.6029 | 3 | 1.6615 | 3 | | | 1.5519 | 2 | 1.3903 | 4 | 1.7444 | 2 |
| 1.4896 | 2 | 1.6544 | 3 | | | 1.4531 | 4 | | | 1.6605 | 4 |
| 1.4530 | 5 | 1.6501 | 3 | | | 1.4432 | 2 | | | 1.6522 | 3 |
| 1.4359 | 3 | 1.4807 | 3 | | | 1.4361 | 3 | | | 1.6168 | 2 |
| 1.4151 | 2 | 1.4539 | 4 | | | 1.4130 | 2 | | | 1.6040 | 2 |
| 1.3854 | 0 | 1.4377 | 4 | | | 1.3852 | 0 | | | 1.5557 | 2 |
| 1.3521 | 2 | 1.4149 | 4 | | | 1.3547 | 2 | | | 1.5108 | 2 |
| | | 1.4046 | 3 | | | 1.3524 | 2 | | | 1.4923 | 2 |
| | | 1.3864 | 4 | | | | | | | 1.4541 | 4 |
| | | 1.3738 | 4 | | | | | | | 1.4378 | 3 |
| | | 1.3556 | 3 | | | | | | | 1.4031 | 2 |
| | | | | | | | | | | 1.3872 | 3 |
| | | | | | | | | | | 1.3557 | 2 |
| | | | | | | | | | | 1.3538 | 2 |

TABLE 4-continued

| Example 1 | | Example 2 | | Example 3 | | Example 4 | | Example 5 | | Example 6 | |
|---|---|---|---|---|---|---|---|---|---|---|---|
| d(Å) | 4.2354 | d(Å) | I/I° | d(Å) | I/I° | d(Å) | I/I° | d(Å) | I/I° | d(Å) | I/I° |
| | | | | | | | | | | 1.3517 | 2 |

TABLE 5

| Examples | Aerosil g | $H_3BO_3$ g | $SiO_2/B_2O_3$ employed | NaOH g | % $SiO_2$ found | % $B_2O_3$ found | $SiO_2/B_2O_3$ found | % Na found |
|---|---|---|---|---|---|---|---|---|
| 7 | 80 | 7.6 | 22 | 7.35 | 90.1 | 4.65 | 22.6 | 3.08 |
| 8 | 80 | 3.6 | 44 | 3.7 | 94.9 | 0.78 | 142.5 | 1.05 |

EXAMPLE 9

A mixture of 60 parts of the ZBH borosilicate zeolite prepared in Example 2, using diethylene glycol dimethyl ether, and 40 parts of boehmite is extruded and subjected to exchange in 20% strength $NH_4Cl$ solution, in a ratio of 1:15, for 2 hours at 80° C.

80% strength methanol is 100% converted at 450° C. at a weight hourly space velocity of 7.8 $h^{-1}$. The yields, based on $CH_2$ employed, are:

| | % |
|---|---|
| $CH_4$ | 1.5 |
| $C_2H_4$ | 4.1 |
| $C_2H_6$ | 0.1 |
| $C_3H_6$ | 25.0 |
| $C_3H_8$ | 0.8 |
| $C_4$ hydrocarbons | 17.6 |
| $C_5$ hydrocarbons | 46.7 |

We claim:

1. A process for the preparation of crystalline ZBH borosilicate zeolites of the pentasil type which comprises: adding silicon dioxide, boric acid and an alkali metal salt to a liquid ether or ether-water solvent wherein the ether is selected from the group consisting of monoethylene, diethylene, triethylene and tetraethylene glycol dimethyl ether, diethyl ether, a mixture of triethylene to decaethylene glycol methyl isopropyl ethers, diethylene glycol methyl isopropyl ether, a mixture of polyethylene glycol methyl isopropyl ethers, a mixture of oxyethylated oxoalcohols having a mean molecular weight of 200, 600 or 6,000, and dimethoxymethane, the molar ratio of $SiO_2$ to $B_2O_3$ being from 3 to 300, the molar ratio of alkali metal salt to $B_2O_3$ being from 1 to 3 and the molar ratio of ether to $B_2O_3$ being from 18 to 390, and thereafter heating the resultant solution to a temperature of from 80° to 140° C. in a closed vessel under autogenous pressure to form said ZBH borosilicate zeolites, wherein the zeolites have the formula $$M_{2/n}O:B_2O_3:x\ SiO_2:y\ H_2O$$

where N is one or more cations of valency n, x is $\geq 10$ and y is from 0 to 80.

2. The process of claim 1, wherein the process takes place in a stirred autoclave under autogenous pressure.

3. The process of claim 1, wherein the solution is heated at from 80° to 140° C. for a period of from 5 to 7 days.

4. The process of claim 1, wherein the solution is heated to a temperature of from 110° to 130° C.

5. The process of claim 1, wherein the molar ratio of $SiO_2$ to $B_2O_3$ is from 10 to 50.

6. The process of claim 1, wherein the molar ratio of alkali metal salt to $B_2O_3$ is from 1.3 to 2.

7. The process of claim 1, wherein the solvent used is diethylene glycol dimethyl ether or a mixture thereof with water.

8. The process of claim 1, wherein the solvent used for the crystallization is triethylene glycol dimethyl ether or a mixture thereof with water.

* * * * *

UNITED STATES PATENT AND TRADEMARK OFFICE
CERTIFICATE OF CORRECTION

PATENT NO. : 4,554,142

DATED : November 19, 1985

INVENTOR(S) : Wolfgang HOELDERICH et al.

It is certified that error appears in the above—identified patent and that said Letters Patent is hereby corrected as shown below:

IN THE CLAIMS:

Claim 1, column 8, line 26, should read

--where M is one or more cations-- rather than

"where N is one or more cations".

Signed and Sealed this

Third Day of March, 1987

Attest:

DONALD J. QUIGG

Attesting Officer

Commissioner of Patents and Trademarks